United States Patent [19]

Malamas et al.

[11] Patent Number: 5,677,342

[45] Date of Patent: Oct. 14, 1997

[54] PHENOXY ACETIC ACIDS AS ALDOSE REDUCTASE INHIBITORS AND ANTIHYPERGLYCEMIC AGENTS

[75] Inventors: Michael S. Malamas, Jamison, Pa.; Iwan Guanwan, Somerset, N.J.

[73] Assignee: American Home Products Corporation, Madison, N.J.

[21] Appl. No.: 701,144

[22] Filed: Aug. 21, 1996

Related U.S. Application Data

[60] Provisional application No. 60/002,855, Aug. 28, 1995.

[51] Int. Cl.$^6$ .................................................. A61K 31/19
[52] U.S. Cl. ............................................ 514/569; 562/462
[58] Field of Search ............................ 514/569; 562/462

[56] References Cited

U.S. PATENT DOCUMENTS

| | | | |
|---|---|---|---|
| 4,897,405 | 1/1990 | Alessi et al. | 514/404 |
| 5,183,825 | 2/1993 | Kees | 514/404 |
| 5,399,588 | 3/1995 | Malamas | 562/462 |
| 5,552,441 | 9/1996 | Dillard et al. | 514/569 |

FOREIGN PATENT DOCUMENTS

| | | | |
|---|---|---|---|
| 0074628 | 3/1983 | European Pat. Off. | C07C 175/00 |
| 3261778 | 9/1990 | Japan | A61K 31/34 |

OTHER PUBLICATIONS

Pazur et al., J. Chem. Soc., 1957, pp. 625–628.
Chen and Joullie, Tetrahetron Letters 23(44), pp. 4567–4568, 1982.

*Primary Examiner*—James H. Reamer
*Attorney, Agent, or Firm*—R. F. Boswell, Jr.

[57] ABSTRACT

This invention relates to 4-formyl-2-(naphthalenylmethyl) phenoxyacetic acids and pharmaceutically acceptable salts thereof according to formula I below, pharmaceutical compositions thereof, a method of treating hyperglycemia due to non-insulin dependent diabetes mellitus, and a method of prevention or treatment of complications associated with diabetes.

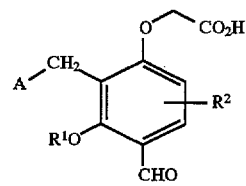

wherein the group A is selected from the group consisting of 1-naphthyl, 2-naphthyl, optionally substituted with alkyl of from one to six carbon atoms, fluorine, chlorine, bromine, iodine, trifluoromethyl, alkoxy of from one to six carbon atoms; $R^1$ is hydrogen or alkyl of from one to six carbon atoms; $R^2$ is selected from hydrogen, fluorine, chlorine, bromine, iodine, alkyl of from one to six carbon atoms, alkoxy of from one to six carbon atoms, and hydroxyl; or a pharmaceutically acceptable metal salt thereof.

14 Claims, No Drawings

PHENOXY ACETIC ACIDS AS ALDOSE REDUCTASE INHIBITORS AND ANTIHYPERGLYCEMIC AGENTS

This application claims the benefit of U.S. provisional application Ser. No. 60/002855 filed Aug. 28, 1995.

FIELD OF THE INVENTION

This invention relates to 4-formyl-2-(naphthalenylmethyl)phenoxyacetic acids and pharmaceutically acceptable salts thereof according to formula I below, pharmaceutical compositions thereof, a method of treating hyperglycemia due to non-insulin dependent diabetes mellitus, and a method of prevention or treatment of complications associated with diabetes.

BACKGROUND OF THE INVENTION

Diabetes mellitus is a syndrome characterized by abnormal insulin production, increased urinary output and elevated blood glucose levels. There are two major subclasses of diabetes mellitus. One is the insulin-dependent diabetes mellitus (IDDM or Type I), formerly referred to as juvenile onset diabetes since it was evident early in life, and non-insulin dependent diabetes mellitus (NIDDM or Type II), often referred to as maturity-onset diabetes. Exogenous insulin by injection is used clinically to control diabetes but suffers from several drawbacks. Insulin is a protein and thus cannot be taken orally due to digestion and degradation but must be injected. It is not always possible to attain good control of blood sugar levels by insulin administration. Insulin resistance sometimes occurs requiring much higher doses of insulin than normal. Another shortcoming of insulin is that while it may control hormonal abnormalities, it does not always prevent the occurrence of complications such as neuropathy, retinopathy, cataracts, glomerulosclerosis, or vascular disorders.

The long-term complications of diabetes develop in tissues where glucose uptake is independent of insulin. In these tissues, which include the lens, retina, kidney and peripheral nerves, the systemic hyperglycemia of diabetes is rapidly transposed into high tissular concentrations of glucose. In all of these tissues this excess glucose is rapidly metabolized by the sorbitol pathway. The intense diabetes-induced flux of glucose through this pathway appears to initiate a cascade of biochemical alterations which slowly progress to cell dysfunction and structural damage. Aldose reductase, the key enzyme in the sorbitol pathway, reduces glucose to sorbitol at the expense of the cofactor NADPH. In animal models of diabetes, compounds which inhibit aldose reductase have been shown to prevent the biochemical, functional and morphological changes induced by hyperglycemia. Early studies by J. H. Kinoshita and collaborators implicated aldose reductase in the etiology of diabetic cataracts. More recent studies have provided compelling evidence that aldose reductase also plays a significant role in the initiation of diabetic nephropathy, retinopathy and neuropathy (cf McCaleb et at, J. Diab. Comp., 2, 16, 1989; Robison et al, Invest. Ophthalmol. Vis. Sci., 30, 2285, 1989; Notvest and Inserra, Diabetes, 36, 500, 1987.

Orally effective antihyperglycemic agents are used to reduce blood glucose levels and to reduce damage to the nervous, retinal, renal or vascular systems through mechanisms affecting glucose metabolism. Such agents act in a variety of different mechanisms including inhibition of aldose reductase, inhibition of fatty acid oxidation, α-glycosidase inhibition, antagonism of $\alpha_2$-receptors and inhibition of gluconeogenesis.

Two classes of compounds have predominated: the biguanides as represented by phenformin and the sulfonylureas as represented by tolbutamide (Orinase®). A third class of compounds which has shown antihyperglycemic activity are thiazolidinediones of which ciglitazone is the prototype. Ciglitazone suppresses the symptoms of diabetes—hyperglycemia, hypertriglyceridemia and hyperinsulinemia [Diabetes 32, 804–10 (1983)].

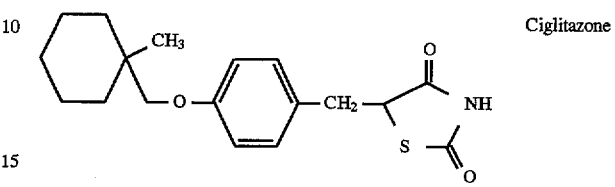

Ciglitazone

Still another class of antihyperglycemic agents are the N-arylalkyl-N-hydroxy ureas and the 2-(arylalkyl)-[1,2,4] oxadiazolidine-3,5-diones. The published PCT patent application WO 92/03425 discloses compounds of the formula:

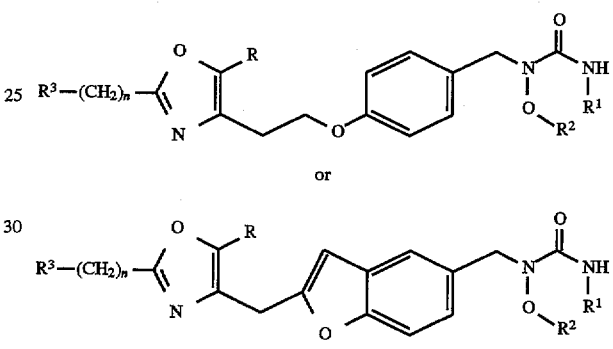

where $R^1$ and $R^2$ are independently H, $C_1$–$C_9$ alkyl, $C_3$–$C_7$ cycloalkyl, phenyl, etc. or $R^1$ and $R^2$ together are carbonyl, which have utility as hypoglycemic or hypocholesteremic agents. The hypoglycemic properties of these compounds in ob/ob mice are discussed by Goldstein et al. J. Med. Chem. 36, 2238–2240 (1993).

4-(Benzofuran-3ylcarbonyl)-phenoxyalkanoic acids having uricosuric utility are disclosed in the Japanese patent JO 3261-778-A. Derivatives of the antibiotic ascochlorin having the formula

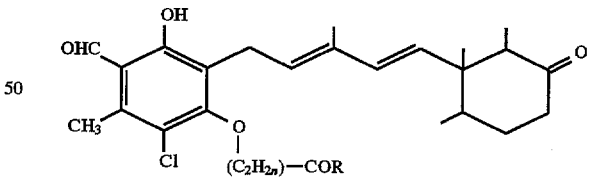

are disclosed in the European Patent application EP 0074628 as being useful for treating diabetes.

SUMMARY OF THE INVENTION

Compounds encompassed by formula (I) have demonstrated oral antihyperglycemic activity in diabetic (ob/ob and db/db) mice, genetic animal models of non-insulin-dependent diabetes mellitus (NIDDM), and aldose reductase inhibitory activity, which renders them beneficial for the prevention or treatment of complications associated with diabetes mellitus.

The phenoxy acetic acids of the present invention are represented by formula (I)

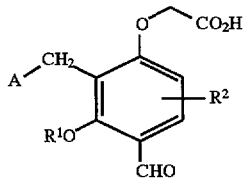

wherein the group A is selected from the group consisting of 1-naphthyl, 2-naphthyl, optionally substituted with alkyl of from one to six carbon atoms, fluorine, chlorine, bromine, iodine, trifluoromethyl, alkoxy of from one to six carbon atoms; $R^1$ is hydrogen or alkyl of from one to six carbon atoms; $R^2$ is selected from hydrogen, fluorine, chlorine, bromine, iodine, alkyl of from one to six carbon atoms, alkoxy of from one to six carbon atoms, and hydroxyl; and the pharmaceutically acceptable salts thereof.

In the above definitions of variable substituents, the terms "alkyl of from one to six carbons" and "alkoxy of from one to six carbons" encompass both straight and branched chain hydrocarbons. Pharmaceucially acceptable salts of the invention compounds include the sodium, potassium, calcium or magnesium salts derived from reaction of an invention phenoxyacetic acid with a metal hydroxide or oxide such as sodium, potassium, calcium or magnesium hydroxides or oxides.

The most preferred compounds of the present invention are:
[2-chloro-6-(5-chloro-naphthalen-2-ylmethyl)-4-formyl-5-hydroxy-3-methyl-phenoxy]-acetic acid,
(4-formyl-3-hydroxy-2-naphthalen-2-ylmethyl-phenoxy)-acetic acid,
(4-formyl-3-hydroxy-2-naphthalen-1-ylmethyl-phenoxy)-acetic acid,
[2-(5-chloro-naphthalen-2-ylmethyl)-4-formyl-3-hydroxy-phenoxy]-acetic acid,
[2-(5-bromo-naphthalen-2-ylmethyl)-4-formyl-3-hydroxy-phenoxy]-acetic acid,
[2-(1-bromo-naphthalen-2-ylmethyl)-4-formyl-3-hydroxy-phenoxy]-acetic acid,
[2-(5-chloro-naphthalen-2-ylmethyl)-4-formyl-3-methoxy-phenoxy]-acetic acid,
[2-(5-chloro-naphthalen-2-ylmethyl)-4-formyl-3-hydroxy-5-methoxy-phenoxy]-acetic acid,
[2-(5-chloro-naphthalen-2-ylmethyl)-4-formyl-3-hydroxy-5-methyl-phenoxy]-acetic acid, and
[6-chloro-2-(5-chloro-naphthalen-2-ylmethyl)-4-formyl-3-hydroxy-phenoxy]-acetic acid.

DETAILED DESCRIPTION OF THE INVENTION

The compounds of the present invention can be prepared according to the following representative synthetic schemes I and II using procedures known to those skilled in the art of organic synthesis.

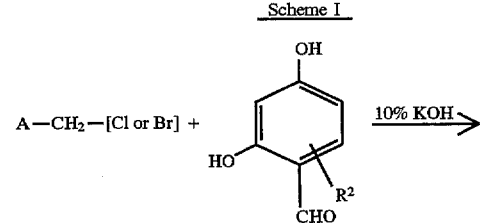

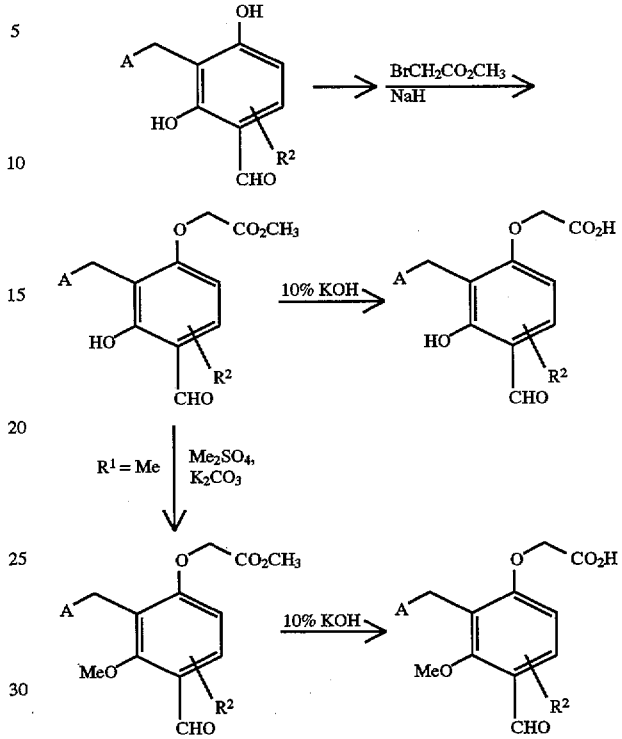

wherein A, $R^1$, $R^2$ are as defined above.

The required substituted resorcinols used in scheme I can be obtained by known methods conventional in the an (Tetrahedron Letters 23, 1982, 4567–4568; J. Chem. Society, 1957, 625–628; Japan Patent JP03261778 A2, 1991), as illustrated in the reaction shown in Scheme II.

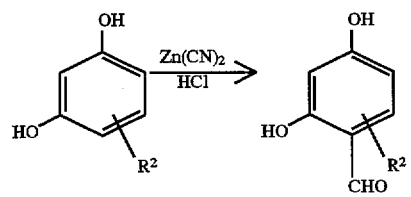

The following examples are included to illustrate the synthetic methods of this invention and shall not be construed to be limiting to the scope of this disclosure.

EXAMPLE 1

[2-chloro-6-(5-chloro-naphthalen-2-ylmethyl)-4-formyl-5-hydroxy-3-methyl-phenoxy]-acetic Acid Step a) 4-chloro-6-(5-chloro-naphthalen-2-ylmethyl)-2-formyl-5-hydroxy-3-methyl-phenol 5-Chloro-2-chloromethylnaphthalene (prepared according to procedures disclosed in our commonly owned U.S. Pat. Nos. 4,897,405 and 5,183,825; 2.48 g, 11.7 mmol) was added portionwise into a cold (0° C.) solution of 4-chloro-2-formyl-5-hydroxy-3-methyl-phenol (prepared according to the procedure disclosed in Tetrahedron Letters 23, 1982, 4567–4568; 2.0 g, 10.6 mmol) and KOH (10%, 10 mL). The mixture was warmed to 45° C. and stirred for 12 hours. The reaction solution was then cooled to room temperature, acidified with HCL (2N), and extracted with EtOAc. The organic extracts were dried over $MgSO_4$. Evaporation and purification by flash chromatography on silica gel (eluting solvent hexane/EtOAc 3/1), gave a light yellow solid (0.65 g, 37% yield, m.p. 179°–181° C.).

Analysis for: $C_{19}H_{14}Cl_2O_3$: Calc'd: C, 63.18; H, 3.91 Found: C, 63.31; H, 4.11

Step b) [2-chloro-6-(5-chloro-naphthalen-2-ylmethyl)-4-formyl-5-hydroxy-3-methyl-phenoxy]-acetic acid methyl ester Sodium hydride (0.46 g, 15.4 mmol) was added dropwise into a solution of 4-chloro-6-(5-chloro-naphthalen-2-ylmethyl)-2-formyl-5-hydroxy-3-methyl-phenol (4.0 g, 11.0 mmol) and N,N-dimethylformamide (75 mL). After stirring for 1 hour, methyl bromoacetate (1.15 mL, 12.18 mmol) was added dropwise. The reaction mixture was warmed to 40° C. and stirred for 12 hours. The reaction solution was then cooled to room temperature, poured into water, acidified with HCl (2N), and extracted with EtOAc. The organic extracts were dried over $MgSO_4$. Evaporation and purification by flash chromatography on silica gel (eluting solvent hexane/EtOAc 10/1), gave an off-white solid (1.14 g, 24% yield, m.p. 115°–116° C.).

Analysis for: $C_{22}H_{18}Cl_2O_5$: Calc'd: C, 60.99; H, 4.19 Found: C, 60.90; H, 4.07

Step c) [2-chloro-6-(5-chloro-naphthalen-2-ylmethyl)-4-formyl-5-hydroxy-3-methyl-phenoxy]-acetic acid Aqueous potassium hydroxide (10%, 2.7 mL) was added in to a solution of [2-chloro-6-(5-chloro-naphthalen-2-ylmethyl)-4-formyl-5-hydroxy-3-methyl-phenoxy]-acetic acid methy ester (1.14 g, 2.63 mmol), THF(15 mL) and MeOH (15 mL). The mixture was stirred for 1 hour, poured into water, acidified with HCl (2N), and extracted with EtOAc. The organic extracts were dried over $MgSO_4$. Evaporation and crystallization from hexane/EtOAc, gave a light yellow solid (0.65 g, 60% yield, m.p. 194°–196° C.).

Analysis for: $C_{21}H_{16}Cl_2O_5$: Calc'd: C, 60.16; H, 3.85 Found: C, 60.30; H, 4.10

EXAMPLE 2

(4-formyl-3-hydroxy-2-naphthalen-2-ylmethyl-phenoxy)-acetic Acid

The title compound was prepared in substantially the same manner as described in example 1. Starting materials 4-hydroxy-2-formyl-phenol and 2-chloromethylnaphthalene were used in place of 4-chloro-2-formyl-5-hydroxy-3-methyl-phenol and 5-chloro-2-chloromethylnaphthalene, respectively. The title compound was obtained as a white solid, m.p. 190°–191° C.

Analysis for: $C_{20}H_{16}O_5$: Calc'd: C, 71.42; H, 4.79 Found: C, 71.10; H, 4.67

EXAMPLE 3

(4-formyl-3-hydroxy-2-naphthalen-1-ylmethyl-phenoxy-acetic Acid

The title compound was prepared in substantially the same manner as described in example 1. Starting materials 4-hydroxy-2-formyl-phenol and 1-chloromethylnaphthalene were used in place of 4-chloro-2-formyl-5-hydroxy-3-methyl-phenol and 5-chloro-2-chloromethylnaphthalene, respectively. The title compound was obtained as a white solid, m.p. 120°–121° C.

Analysis for: $C_{20}H_{16}O_5$: Calc'd: C, 71.42; H, 4.80 Found: C, 71.89; H, 5.17

EXAMPLE 4

[2-(5-chloro-naphthalen-2-ylmethyl)-4-formyl-3-hydroxy-phenoxy]-acetic Acid

The title compound was prepared in substantially the same manner as described in example 1. Starting material 4-hydroxy-2-formyl-phenol was used in place of 4-chloro-2-formyl-5-hydroxy-3-methyl-phenol. The title compound was obtained as a white solid, m.p. 156°–157° C.

Analysis for: $C_{20}H_{15}ClO_5$: Calc'd: C, 64.78; H, 4.08 Found: C, 64.68; H, 3.92

EXAMPLE 5

[2-(5-bromo-naphthalen-2-ylmethyl)-4-formyl-3-hydroxy-phenoxy]-acetic Acid

The title compound was prepared in substantially the same manner as described in example 1. Starting materials 4-hydroxy-2-formyl-phenol and 5-bromo-2-chloromethylnaphthalene were used in place of 4-chloro-2-formyl-5-hydroxy-3-methyl-phenol and 5-chloro-2-chloromethylnaphthalene, respectively. The title compound was obtained as a white solid, m.p. 120°–121° C.

Analysis for: $C_{20}H_{15}BrO_5$: Calc'd: C, 57.85; H, 3.64 Found: C, 58.34; H, 3.59

EXAMPLE 6

[2-(1-bromo-naphthalen-2-ylmethyl)-4-formyl-3-hydroxy-phenoxy]-acetic Acid

The title compound was prepared in substantially the same manner as described in example 1. Starting material 4-hydroxy-2-formyl-phenol and 1-bromo-2-chloromethylnaphthalene were used in place of 4-chloro-2-formyl-5-hydroxy-3-methyl-phenol and 5-chloro-2-chloromethylnaphthalene, respectively. The title compound was obtained as a white solid, m.p. 165°–166° C.

Analysis for: $C_{20}H_{15}BrO_5$: Calc'd: C, 57.85; H, 3.64 Found: C, 58.04; H, 3.58

EXAMPLE 7

[2-(5-chloro-naphthalen-2-ylmethyl)-4-formyl-3-methoxy-phenoxy]-acetic Acid

Dimethyl sulfate (0.54 g, 4.3 mmol) was added dropwise into a mixture of [2-chloro-6-(5-chloro-naphthalen-2-ylmethyl)-4-formyl-5-hydroxy-3-methyl-phenoxy]-acetic acid methyl ester (0.76 g, 2.05 mmol), potassium carbonate (0.65 g, 4.8 mmol) and acetone (75 mL). The mixture was refluxed for 2 hours, poured into water, acidified with HCl (2N) and extracted with EtOAc. The organic extracts were dried over $MgSO_4$. Evaporation gave a yellow oil, which was dissolved in MeOH (15 mL), THF (15 mL) and treated with KOH (10%, 3.1 mL). After stirring for 4 hours the mixture was poured into water, acidified with HCl (2N), and extracted with EtOAc. The organic extracts were dried over $MgSO_4$. Evaporation and crystallization from hexane/EtOAc, gave an off-white solid (0.34 g, 43% yield, m.p. 191°–192° C.).

Analysis for: $C_{21}H_{17}ClO_5$: Calc'd: C, 65.54; H, 4.45 Found: C, 65.34; H, 4.44

EXAMPLE 8

[2-(5-chloro-naphthalen-2-ylmethyl)-4-formyl-3-hydroxy-5-methoxy-phenoxy]-acetic Acid The title compound was prepared in substantially the same manner as described in example 1. Starting material 4-hydroxy-2-formyl-3-methoxy-phenol was used in place of 4-chloro-2-formyl-5-hydroxy-3-methyl-phenol. The title compound was obtained as a white solid, m.p. 237°–238° C.

Analysis for: $C_{21}H_{17}ClO_6$: Calc'd: C, 62.93; H, 4.27 Found: C, 63.03; H, 4.21

EXAMPLE 9

[2-(5-chloro-naphthalen-2-ylmethyl)-4-formyl-3-hydroxy-5-methyl-phenoxy]-acetic Acid The title compound was prepared in substantially the same manner as described in example 1. Starting material 4-hydroxy-2-formyl-3-methyl-phenol was used in place of 4-chloro-2-formyl-5-hydroxy-3-methyl-phenol. The title compound was obtained as a white solid, m.p. 191°–192° C.

Analysis for: $C_{21}H_{17}ClO_5$: Calc'd: C, 65.55; H, 4.45 Found: C, 65.37; H, 4.44

EXAMPLE 10

[6-chloro-2-(5-chloro-naphthalen-2-ylmethyl)-4-formyl-3.hydroxy-phenoxy]-acetic Acid The title compound was prepared in substantially the same manner as described in example 1. Starting material 4-chloro-2-formyl-5-hydroxy-phenol was used in place of 4-chloro-2-formyl-5-hydroxy-3-methyl-phenol. The title compound was obtained as a white solid, m.p. 210°–211° C.

Analysis for: $C_{20}H_{14}Cl_2O_5$: Calc'd: C, 59.28; H, 3.48 Found: C, 58.95; H, 3.44

PHARMACOLOGY

I. In vitro Inhibition of Aldose Reductase in the Bovine Lens

The aldose reductase inhibiting effects of the compounds of formula I were tested by employing an in vitro testing procedure similar to that described by S. Hayman and J. H. Kinoshita, J. Biol. Chem., 240, 877 (1965) wherein the abilitty of the invention compounds to inhibit bovine lens aldose reductase with DL-glyceraldehyde as the substrate was determined. In the present case the procedure of Hayman and Kinoshita was modified in that the final chromatography step was omitted in the preparation of the enzyme from bovine lens. The results for compounds of this invention tested in this assay are presented in Table 1.

TABLE 1

| Compound of Example No. | Dose (M) | % Inhibition of aldose reductase |
|---|---|---|
| 1 | $4 \times 10^{-8}$ | 49 |
| 2 | $10^{-7}$ | 34 |
| 3 | $10^{-6}$ | 53 |
| 4 | $4 \times 10^{-8}$ | 78 |
| 5 | $4 \times 10^{-8}$ | 84 |
| 6 | $4 \times 10^{-8}$ | 78 |
| 7 | $4 \times 10^{-8}$ | 83 |
| 8 | $4 \times 10^{-8}$ | 81 |
| 9 | $4 \times 10^{-8}$ | 89 |
| 10 | $10^{-7}$ | 36 |

2. Determination of Blood Glucose Lowering in Diabetic db/db Mice.

On the morning of Day 1, 35 mice [male diabetic db/db (C57BL/KsJ) mice (Jackson Laboratories), 2–7 months of age and 50–70 g] were fasted for 4 hours, weighed and a baseline blood sample (15–30 μl) was collected from the tail-tip of each mouse without anesthesia, and placed directly into a fluoride-containing tube, mixed and maintained on ice. Food was then returned to the mice. The plasma was separated and levels of glucose in plasma determined by the Abbott VP Analyzer. Because of the variable plasma glucose levels of the db/db mice, 5 mice having the most extreme (i.e., highest or lowest) plasma glucose levels were excluded and the remaining 30 mice were randomly assigned into 7 groups of equivalent mean plasma glucose levels (N=6 for vehicle and N=4 for each drug group). On the afternoon of Days 1, 2 and 3, the vehicle, control or test drugs were administered (p.o.) to the ad libitum fed mice. On the morning of Day 4, the mice were weighed and food removed, but water was available ad libitum. Three hours later, a blood sample was collected and then the mice were given the fourth administration of drug or vehicle. Blood samples were collected again from the unanesthetized mice at 2 and 4 hours after drug administration. The plasma was separated and levels of glucose in plasma was determined by the Abbott VP Analyzer.

For each mouse, the percent change of its plasma glucose level on Day 4 (mean of the 2 and 4 hr samples) from respective level before drug administration (Day 1 baseline sample) is determined as follows:

$$\frac{\text{mean of 2 and 4 hr samples (Day 4)}}{\text{Baseline Sample (Day 1)}} \times 100$$

Analysis of variance followed by Dunnett's multiple comparison (one-sided) will be used to estimate the 'degree of statistical significance of the difference between the vehicle control group and the individual drug-treated groups. A drug will be considered active, at the specific dosage administered, if the difference of the plasma glucose level has a $p<0.05$.

The positive control, ciglitazone produces a 18 to 34% (26% average) decrease in plasma glucose levels at 100 mg/kg/day×4 days, p.o. The compounds of examples 1 and 2 are comparable with the results for ciglitazone as shown in Table 2.

TABLE 2

| Compound of Example No. | Dose mg/kg, p.o. | % Change glucose |
|---|---|---|
| 1 | 100 | −19 |
| 2 | 100 | −23 |

The diabetic db/db (C57BL/KsJ) mouse exhibits many metabolic abnormalities that are associated with non-insulin dependent diabetes mellitus (Type II) in humans. The animals are obese, glucose intolerant and have fasting hyperglycemia which is sometimes accompanied by a paradoxical hyperinsulinemia (1). Furthermore, the db/db mouse will eventually develop some of the long-term complications that have been associated with diabetes mellitus (1). In spite of these commonalities, the acute administration of sulfonylureas (even at extremely high doses) will not reduce the hyperglycemia of the db/db mouse (2). The ability of a few other hypoglycemic agents to be effective in this species suggest that the other agents have mechanism of action which are different from that of the sulfonylureas (2,3,4,5). Such compounds, therefore, are more likely to be efficacious in the population of type II diabetic patients that do not respond to sulfonylurea therapy.

References:

1. Coleman, D. L. (1982) Diabetes-obesity syndromes in mice. Diabetes 31 (Suppl. 1); 1–6.
2. Tutwiler, G. F., T. Kirsch, and G. Bridi (1978). A pharmacologic profile of McN-3495 [N-(1-methyl-2- pyrrolidinylidene)-N'-phenyl-1-pyrrolidine-carboximidamide], a new, orally effective hypoglycemic agent. Diabetes 27:856–857.

3. Lee, S.M., G. Tutwiler, R. Bressler, and C. H. Kircher (1982). Metabolic control and prevention of nephropathy by 2-tetradecylglycidate in the diabetic mouse (db/db). Diabetes 31:12–18.

4. Chang, A. Y., B. W. Wyse, B. I. Gilchrist, T. Peterson, and R. Diani (1983) Ciglitazone, a new hypoglycemic agent. 1. Studies in ob/ob and db/db mice, diabetic Chinese hamsters, and normal and streptozocin-diabetic rats. Diabetes 32: 830–838.

5. Hosokawa, T., K. Ando, and G. Tamura (1985). An ascochlorin derivative, AS-6, reduces insulin resistance in the genetically obese diabetic mouse, db/db. Diabetes 34: 267–274.

3. Determination of Blood Glucose Lowering Effect in ob/ob mice

The non-insulin-dependent diabetic syndrome can be typically characterized by obesity, hyperglycemia, abnormal insulin secretion, hyperinsulinemia and insulin resistance. The genetically obese-hyperglycemic oh/oh mouse exhibits many of these metabolic abnormalities and is thought to be a useful media to search for hypoglycemic agents to treat NIDDM (Coleman, 1978)

Male or female ob/ob mice (C57B1/6J), ages 2 to 5 months (10 to 65 g), of a similar age are randomized according to plasma glucose into 4 groups of 10 mice. The mice are housed 5 per cage and are maintained on normal rodent chow with water ad libitum. The mice receive test compound daily. The test compound is suspended in 0.5 mL of 0.5% methyl cellulose and is administered by gavage (dissolved in drinking water) or admixed in the diet. The dose of compound given ranges from 2.5 to 200 mg/kg/day. Body weight of fed animals is measured at the beginning of each week and doses for the entire week are calculated using this weight and are expressed in terms of the active moiety of the compound. Control mice receive vehicle only.

On the morning of Days 4, 7 or 14 two drops of blood (approximately 50 µl) are collected into sodium fluoride containing tubes either from the tail vein or after decapitation. For those studies in which the compound is administered daily by gavage, the blood samples are collected four hour after compound administration. The plasma is isolated by centrifugation and the concentration of glucose is measured enzymatically on an Abbott V. P. Analyzer and the plasma concentration of insulin is determined by radioimmunoassay (Heding, 1972). For each mouse, the percentage change in plasma glucose on Day 4, 7 or 14 is calculated relative to the mean plasma glucose of the vehicle treated mice. Analysis of variance followed by Dunnett's Comparison Test (one tailed) is used to estimate the significant difference between the plasma glucose values from the control group and the individual compound treated groups. The results are presented in Table 3.

TABLE 3

| Compound of Example No. | Dose mg/kg, p.o. | ob/ob data | |
|---|---|---|---|
| | | % Change glucose | % Change insulin |
| 1 | 100 | −24 | −38 |

References:

1. Brichard, S., Bailey, C. and Henquin, J.: Marked improvement of glucose homeostasis in diabetic ob/ob mice given oral vanadate. Diabetes 39: 1326–1332, 1990.

2. Chang, A., Wyse, B., Gilchrist, B., Peterson, T. and Diani, A.: Ciglitazone, a new hypoglycemic agent. I. Studies in ob/ob and db/db mice, diabetic Chinese hamsters, and normal and streptozoticin-induced diabetic rats. Diabetes 32: 830–838, 1983.

3. Coleman, D.: Obese and diabetes: Two mutant genes causing diabetes-obesity syndromes in mice. Diabetologia 14: 141–148, 1978.

4. Heding, L. G.: Determination of total serum insulin (IRI) in insulin-treated diabetic patients. Diabetologia 8: 260–266, 1972.

PHARMACEUTICAL COMPOSITION

Based on the results of the pharmacological assay, the compounds of this invention are useful in the treatment of hyperglycemia in diabetes mellitus.

The compounds may be administered neat or with a pharmaceutical carrier to a mammal in need thereof. The pharmaceutical carrier may be solid or liquid and the active compound shall be a therapeutically effective amount.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. A dosage range of from 0.1 to 200 mg/kg/day is contemplated, with a preferred dosage of from 0.1 to 100 mg/kg/day. Due to uncertainty in relating laboratory mouse study data to other mammals, the degree of hyperglycemia, and the compound selected, the dosages used in the treatment of non-insulin dependent diabetes mellitus must be subjectively determined by a physician or veterinarian according to standard medical or veterinary practice.

What is claimed is:

1. A compound according to the formula

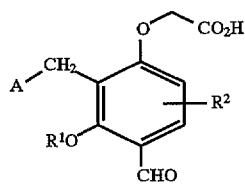

wherein the group A is selected from the group consisting of 1-naphthyl, 2-naphthyl, optionally substituted with alkyl of from one to six carbon atoms, fluorine, chlorine, bromine, iodine, trifluoromethyl, alkoxy of from one to six carbon atoms; $R^1$ is hydrogen or alkyl of from one to six carbon atoms; $R^2$ is selected from hydrogen, fluorine, chlorine, bromine, iodine, alkyl of from one to six carbon atoms, alkoxy of from one to six carbon atoms, and hydroxyl; or a pharmaceutically acceptable metal salt thereof.

2. A compound according to claim 1 which is [2-chloro-6-(5-chloro-naphthalen-2-ylmethyl)-4-formyl-5-hydroxy-3-methyl-phenoxy]-acetic acid.

3. A compound according to claim 1 which is (4-formyl-3-hydroxy-2-naphthalen-2-ylmethyl-phenoxy)-acetic acid.

4. A compound according to claim 1 which is (4-formyl-3-hydroxy-2-naphthalen-1-ylmethyl-phenoxy)-acetic acid.

5. A compound according to claim 1 which is [2-(5-chloro-naphthalen-2-ylmethyl)-4-formyl-3-hydroxy-phenoxy]-acetic acid.

6. A compound according to claim 1 which is [2-(5-bromo-naphthalen-2-ylmethyl)-4-formyl-3-hydroxy-phenoxy]-acetic acid.

7. A compound according to claim 1 which is [2-(1-bromo-naphthalen-2-ylmethyl)-4-formyl-3-hydroxy-phenoxy]-acetic acid.

8. A compound according to claim 1 which is [2-(5-chloro-naphthalen-2-ylmethyl)-4-formyl-3-methoxy-phenoxy]-acetic acid.

9. A compound according to claim 1 which is [2-(5-chloro-naphthalen-2-ylmethyl)-4-formyl-3-hydroxy-5-methoxy-phenoxy]-acetic acid.

10. A compound according to claim 1 which is [2-(5-chloro-naphthalen-2-ylmethyl)-4-formyl-3-hydroxy-5-methyl-phenoxy]-acetic acid.

11. A compound according to claim 1 which is [6-chloro-2-(5-chloro-naphthalen-2-ylmethyl)-4-formyl-3-hydroxy-phenoxy]-acetic acid.

12. A method of treating hyperglycemia of non-insulin dependent diabetes mellitus in mammals which comprises administration thereto of a therapeutically effective amount of a compound of the formula

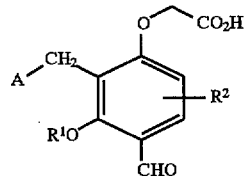

wherein the group A is selected from the group consisting of 1-naphthyl, 2-naphthyl, optionally substituted with alkyl of from one to six carbon atoms, fluorine, chlorine, bromine, iodine, trifluoromethyl, alkoxy of from one to six carbon atoms; $R^1$ is hydrogen or alkyl of from one to six carbon atoms; $R^2$ is selected from hydrogen, fluorine, chlorine, bromine, iodine, alkyl of from one to six carbon atoms, alkoxy of from one to six carbon atoms, and hydroxyl; or a pharmaceutically acceptable metal salt thereof.

13. A method of treating or preventing complications attributed to the hyperglycemia of non-insulin dependent diabetes mellitus in mammals which comprises adminstration thereto of an therapeutically effective amount of a compound of the formula

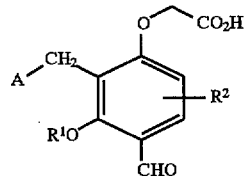

wherein the group A is selected from the group consisting of 1-naphthyl, 2-naphthyl, optionally substituted with alkyl of from one to six carbon atoms, fluorine, chlorine, bromine, iodine, trifluoromethyl, alkoxy of from one to six carbon atoms; $R^1$ is hydrogen or alkyl of from one to six carbon atoms; $R^2$ is selected from hydrogen, fluorine, chlorine, bromine, iodine, alkyl of from one to six Carbon atoms, alkoxy of from one to six carbon atoms, and hydroxyl; or a pharmaceutically acceptable metal salt thereof.

14. A pharmaceutical composition for the treatment of hyperglycemia or diabetic complications in mammals which comprises a pharmaceutically acceptable carrier and a therapeutically effective amount of a compound of the formula

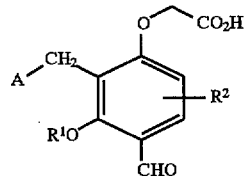

wherein the group A is selected from the group consisting of 1-naphthyl, 2-naphthyl, optionally substituted with alkyl of from one to six carbon atoms, fluorine, chlorine, bromine, iodine, trifluoromethyl, alkoxy of from one to six carbon atoms; $R^1$ is hydrogen or alkyl of from one to six carbon atoms; $R^2$ is selected from hydrogen, fluorine, chlorine, bromine, iodine, alkyl of from one to six carbon atoms, alkoxy of from one to six carbon atoms, and hydroxyl; or a pharmaceutically acceptable metal salt thereof.

* * * * *